United States Patent [19]

Fahlvik et al.

[11] 4,127,384

[45] Nov. 28, 1978

[54] AUTOCLAVE FOR STERILIZING OBJECTS

[75] Inventors: Hans A. Fahlvik, Sloinge; Kurt E. Sandquist, Getinge, both of Sweden

[73] Assignee: Aktiebolaget Electrolux, Stockholm, Sweden

[21] Appl. No.: 762,345

[22] Filed: Jan. 25, 1977

[30] Foreign Application Priority Data

Jan. 26, 1976 [SE] Sweden .............................. 7600740

[51] Int. Cl.² .............................................. A61L 3/00
[52] U.S. Cl. ..................................... 422/109; 422/295
[58] Field of Search ............................... 21/56, 94–98

[56] References Cited

U.S. PATENT DOCUMENTS

| | | | |
|---|---|---|---|
| 1,902,625 | 3/1933 | Dunham ................................... | 21/56 |
| 3,086,837 | 4/1963 | Wilkinson et al. ........................ | 21/94 |
| 3,093,449 | 6/1963 | Kotarski et al. .......................... | 21/56 |
| 3,450,487 | 6/1969 | Wallden .................................... | 21/96 |
| 3,481,688 | 12/1969 | Craig et al. ............................... | 21/94 |
| 3,531,300 | 9/1970 | Greenberg et al. ....................... | 21/94 |
| 3,537,825 | 11/1970 | Adamik ..................................... | 21/94 |
| 3,910,761 | 10/1975 | Hopkins .................................... | 21/94 |
| 4,003,703 | 1/1977 | Montgomery et al. ................... | 21/56 |

FOREIGN PATENT DOCUMENTS 2,363,468  3/1975  Fed. Rep. of Germany .............. 21/94

Primary Examiner—Morris O. Wolk
Assistant Examiner—Bradley Garris
Attorney, Agent, or Firm—Alfred E. Miller

[57] ABSTRACT

An apparatus and method for sterilizing objects, the apparatus being an autoclave having a chamber into which a supply conduit is connected provided with a medium, such as steam and a further supply conduit provided with at least one control medium, such as compressed air. The apparatus also has a discharge conduit and a vent conduit. The apparatus and method achieves the desired results of sterilization of the objects within said chamber by operating the system as near as possible to the temperature tolerance of the plastic packaging of the products being treated. The thermodynamic system utilized is so constructed and arranged to control the temperature in the chamber with great accuracy and to permit trimming of the operation of the system within certain parameters for a given program, or to readjust the system for another program.

7 Claims, 3 Drawing Figures

AUTOCLAVE FOR STERILIZING OBJECTS

BACKGROUND OF THE INVENTION

It is known that sterilization must occur at a temperature which is as high as possible, but yet below a temperature at which there is a risk of damage to the packaging material of the objects to be treated. One example of such goods with packaging material is pharmaceutical products constituting plastic ampoules, such as polypropylene, which has a comparatively low temperature at which softening compounds in the plastic start to diffuse out of the material. In the hottest part of a packaging, which is not in contact with the liquid in the package, the plastic will start shrinking and may become deformed, and cracks may appear. This situation cannot be tolerated with respect to the risk of bacteria growing into the cracks. Therefore, it is a highly desirable object to use the highest possible temperature in the chamber without reaching a temperature which would damage the material in ordder to properly sterilize the packaged product.

Autoclaves for sterilization of products in packages are known but cannot be considered as satisfactory since it is not possible during the sterilization period in these autoclaves to regulate pressure and temperature in the autoclave chamber with such accuracy that the treatment temperature in fact can be kept near the temperature determined by the tolerance of the packaging material. Therefore, a lower temperature than desired is chosen, with the consequence that the sterilization treatment times are very long. On the other hand, if a high temperature is chosen there is the risk of some packaging material being destroyed during the treatment, and as a result the outcome of the treatment has to be carefully controlled.

These known systems for sterilization of objects are based on an intermittent supply to the chamber of the media controlling the process with respect to given criteria. The control of the supply of one of these media is entirely independent of the supply of the other medium and thus, the periods of supply of the media will be upset. For example, this can result in that if the chamber temperature is sufficiently high there will be no supply of steam, so that the pressure will drop and cold compressed air will be supplied. If instead the temperature is too low, but the pressure sufficiently high, only steam will be supplied to the chamber. This steam will enter the system with the total pressure of the entire chamber against it. Due to the character of the control, temperature gradients can appear in the system and even locally in the chamber, because of the impossible task of designing a symmetrical pipe system for affluence and effluence of the chamber. Furthermore, distribution of the temperature gradients to certain locations in the chamber tends also to be dependent on the charge of the autoclave. Considerable research has been undertaken to master this problem, especially after delivery and on trimming of a new plant it has been necessary to spend much work on attempts to achieve improvements. This work has, among other things, included re-dimensioning of the pipe system, particularly in the chamber.

It would be evident from the foregoing that an object of the present invention is to provide a thermodynamic system which can be controlled with great accuracy and permits a constant temperature to be maintained in the entire chamber. Thus, the invention makes it possible to accomplish a given process in this system.

Another object of the present invention is to provide a system which is easy to trim for operation with certain parameter values for a given program or to readjust the system for operation with another program.

A further object of the present invention is to provide a method of achieving a thermodynamic system which can be controlled with great accuracy and maintains a constant temperature in the entire chamber and which the chamber with products therein is heated, after which the working media are caused to flow through the chamber in quantities controlled by regulating valves that are operated by means controlled by the temperature in the steam conduit, and by the pressure and the temperature in the chamber.

Still another object of the present invention is to provide a device for carrying out the method according to the invention and is mainly characterized in that a regulating valve in the steam supply conduit is operated by a regulator controlled by the temperature in the conduit after the valve, while a regulating valve in the air supply conduit is operated by a regulator controlled by the temperature in the chamber. Moreover, the device is provided with a bypass conduit with a valve that is arranged in the compressed air supply conduit, the valve of the bypass conduit being operated by a pressostat controlled by the pressure in the chamber. Furthermore, the vent conduit and the discharge conduit each have a throttle for constant flow therethrough, and the vent conduit further has a valve operated by a regulator controlled by the pressure in the chamber.

In order that the invention will be more clearly understood, it will now be disclosed in greater detail with reference to the accompanying drawings, in which.

DESCRIPTION OF THE PREFERRED EMBODIMENT

Figure 1:
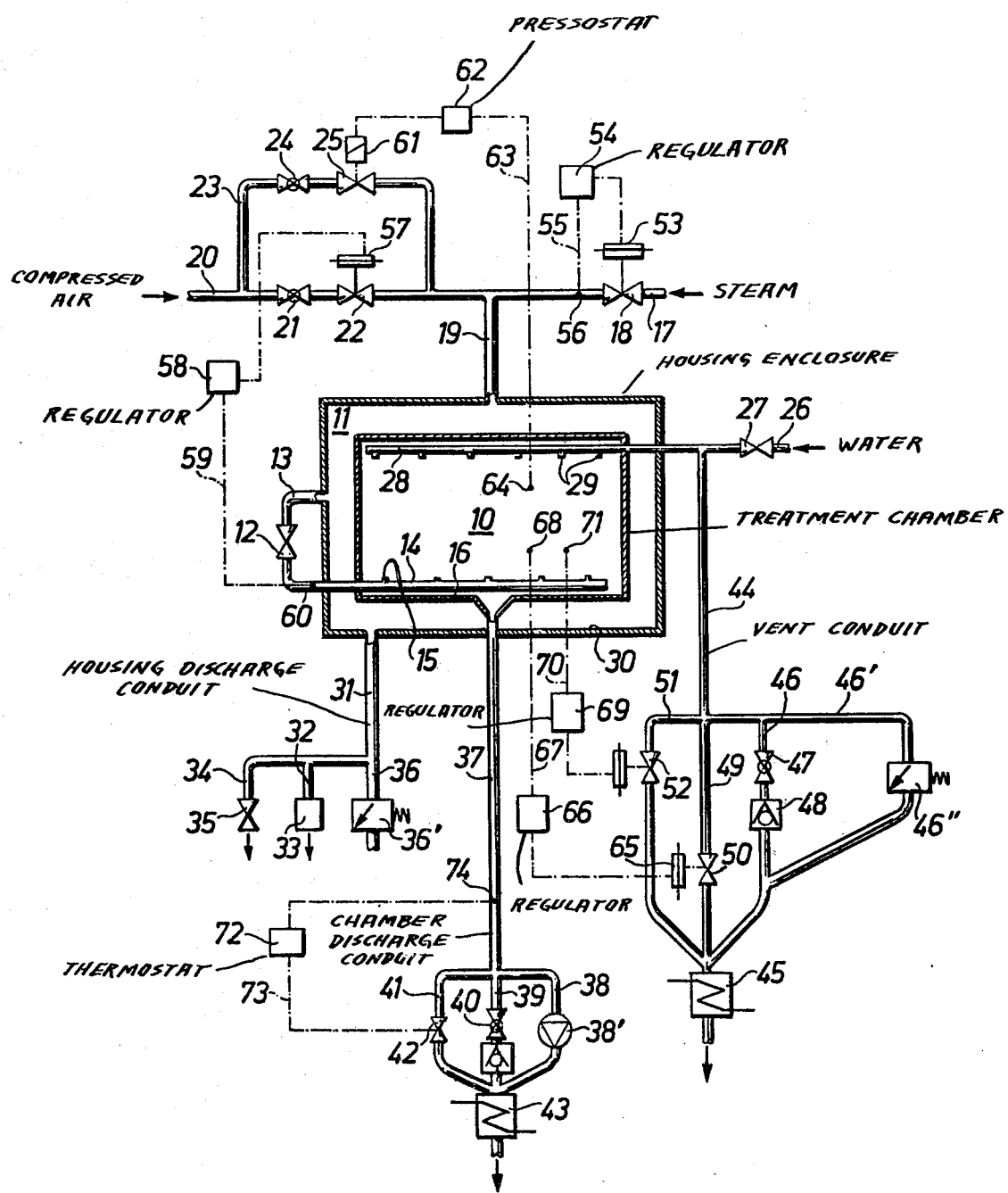
FIG. 1 is a diagrammatic view of an autoclave with valves constructed in accordance with the teachings of the present invention.

The autoclave shown in FIG. 1 has a treatment chamber 10 shrouded by a housing 11 which communicates with the chamber by means of a conduit 13 having a valve 12. The connecting conduit 13 extends generally from the upper part of the housing 11 and opens into the chamber 10 by means of tubes 14 provided with distributing nozzles 15 located at the bottom 16 of the chamber 10.

A conduit 17 with a shut-off valve (not shown) is adapted to conduct steam through a valve 18 into a mixing chamber 19 that communicates directly with the housing 11. A compressed air conduit 20 provided with a shut-off valve (not shown) is connected to the mixing chamber 19 by means of a throttle 21 and a valve 22. The arrangement also has a bypass conduit 23 around the valve 22 which is provided with a throttle 24 and a valve 25.

FIG. 1 also shows a water pipe 26 with a shut-off valve (not shown) and a valve 27, the pipe 26 opening into the upper part of the chamber 10 by means of tubes 28 with distributing nozzles 29.

The present autoclave also has a system by which the working media are let or drawn out. This system comprises a discharge conduit 31 at the bottom 30 of the housing 11 having a branch 32 with a steam trap 33 and a condensate water drain and another parallel branch 34 includes a valve 35. A further branch 36 is shown having a relief valve 36'.

As further seen in FIG. 1, a discharge conduit 37 is connected to the bottom 16 of the chamber 10. The conduit 37 has a branch 38 having a vacuum pump 38' and a branch 39 with a throttle valve 40, as well as a branch 41 having a drain valve 42. All these branches pass through a condenser 43 to an outlet drain. The valve 42 is preferably a piston valve controlled by a thermostat 72 positioned in an impulse conduit 73 communicating with a temperature sensing body 74 in the conduit 37.

The upper part of the chamber 10 has an outlet through which the tubes 28 pass. Part of the pipe 26 and a conduit 44 connected thereto are provided with branches passing through a condenser 45. The outlet conduit 44 from the chamber has a branch 46 with a throttle 47 and a non-return valve 48, a branch 49 with a valve 50, and a branch 51 with a valve 52. In addition, a branch 46' is provided with a relief valve 46".

It should be mentioned that the autoclave has also various known details which are not shown in FIG. 1, for example, safety valves, filters, means for operating the door and sealing means for the door, several measuring devices and, if desired, water tanks for specially treated water for special conditions.

Up to this point the autoclave has been specified in principle without describing the control derices, i.e. for operating the valves.

Figure 2:
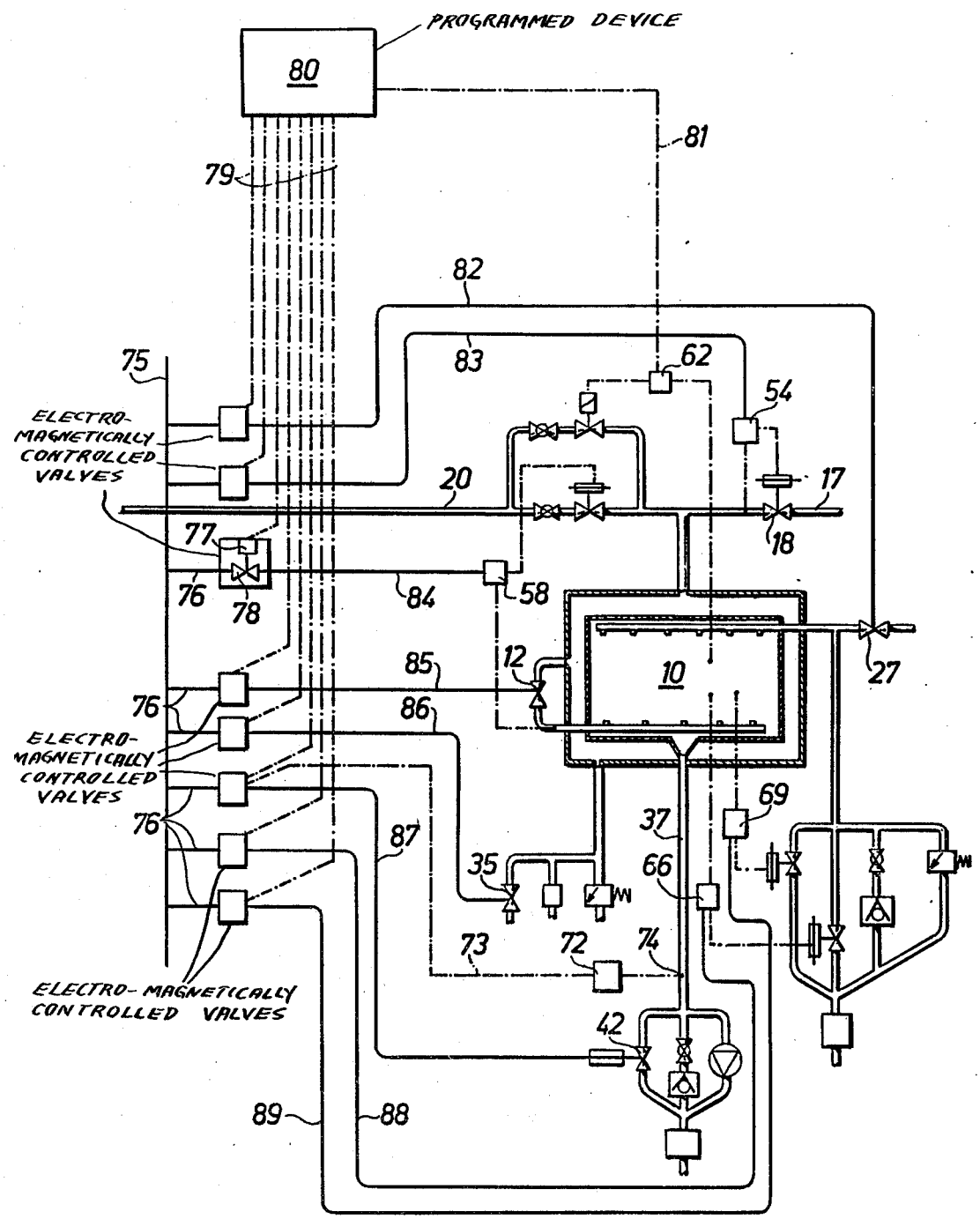
FIG. 2 is the same diagrammatic view as shown in FIG. 1, but on a reduced scale, and with the addition of a control system for the valves.

Referring now to FIG. 2, the control system of the autoclave comprises a supply of compressed air by several electromagnetically controlled valves in conduits to operating devices of the above valves in the conduits for the working media in the autoclave. The electromagnetic valves are operated by a control panel (not shown) together with programmed devices, time control devices, etc.

As seen in FIG. 1, the operating devices 53 of the valve 18 in the steam conduit 17 receives compressed air by a temperature-controlled regulator 54, which receives impulses by a conduit 55 from a sensing body 56 positioned in the conduit 17 in the downstream side after the valve 18.

The valve 22 in the air conduit 20 has an operating device 57 which receives impulses from a temperature-controlled regulator 58 connected to an impulse conduit 59 having a sensing body 60 situated in the connecting conduit 13 between the housing 11 and the chamber 10 immediately ahead of the inlet to the chamber through the tubes 14.

The valve 25 in the second air conduit 23 has an operating device 61 controlled by a pressostat 62 with an impulse conduit 63 connected to a point 64 in the chamber 10. Preferably, the valve 25 is a magnet valve controlled directly by the pressostat.

A valve 50 in the discharge part in the conduit 49 is controlled by a pressure controlled regulator 66 receiving pressure impulses through a conduit 67 from a sensing body 68 in the chamber 10. The valve 52 in the conduit 51 is controlled by a pressure controlled regulator 69, which by means of a conduit 70 sensing the pressure at a point 71 in the chamber 10.

In order to activate the above described regulators 54, 58, 66 and 69, the pressostat 62, and the valves 12, 27, 35 and 42, the apparatus uses a control system which is diagrammatically shown in FIG. 2. It includes a compressed air supply conduit 75 with a multiplicity of branches 76 to valves 78 controlled by electromagnets 77. For the sake of simplicity, only one valve 78 is shown in detail, the others being identical. The electromagnets 77 are connected by conduits 79 to a programmed device 80 which comprises known components, such as time-controlled devices and devices controlled by the condition existing in the autoclave chamber 10. The programmed device can have means to perform different programs, for example, sterilization at 110° C. or at 120° C. When the programmed device 80, by means of a conduit 79, sends an impulse to a valve 78, compressed air is admitted by one or several of the conduits 82–89 to the respective operating device in the conduits for working media to the autoclave. The pressostat 62 is activated directly from the programmed device 80 by electric impulses sent through a conduit 81 and is furthermore controlled by the pressure in the chamber.

As previously stated hereinabove, the drain valve 42 is controlled by the thermostat 72, whose impulse conduit 73 connects to an electromagnet 77 of an air valve in the conduit 87 to the operating device of the valve 42.

In a practical embodiment, regulators of Minneapolis-Honeywell Regulator Company Type PP 97 A for pressure control and Type LP 97 A for temperature conrol have been used in the present apparatus.

The above-described apparatus and arrangement operates as follows:

When the objects to be treated have been placed in the chamber 10, and the autoclave door shut, the valve 18 in the steam conduit 17 is opened so that steam is supplied to the chamber 10 by means of the mixing chamber 19, the housing 11 and the connection conduit 13. In addition to the objects present there is also air in the chamber and this air is expelled through the discharge conduit 37. The valve 52 in outlet 44 does not open until the pressure in the chamber has reached a preset value. Air and condenstate are passed through the valve 42 until the temperature of the mixture has reached a given value and the valve 42 closes while the condensate is expelled through the valve 40. The temperature at which the valve 42 closes is adjustable by means of the thermostat 72. In the first instance, the air is expelled and then steam condenses on the chamber wall and on the objects in the chamber, during which process heat is given off. The temperature in the chamber increases rapidly, and during this heating cycle only steam is supplied. The temperature in the chamber is regulated by pressure-controlled devices, for example, the regulator 69. However, the pressure and the temperature in the chamber 10 will rise and when the pressure in the ampoules, which pressure depends on the temperature therein, has reached a given level an impulse is delivered to the programmed device 80, which operates the system, so that the pressostat 62 is activated and the bypass conduit 23 for compressed air becomes active. Simultaneously, the supply of steam ceases, and after a certain time for venting, the regulators 54 and 58 for supplying steam and air respectively are connected and at the same time the regulator 69 of the discharge valve 52 is disconnected and the regulator 66 in the other discharge valve 50 is connected in its place. During the sterilization period, the condition in the chamber 10 is controlled by the regulators 54 and 58 for the supply of working media and the regulator 66 for the outlet.

The above-mentioned three regulators require special adjustment to form a stable dynamic system. The optimum of this adjustment is in a relatively narrow zone surrounding the given point of operation, i.e. the control accuracy of the system depends on the error variations relative to a given point. The invention proposes a separate auxiliary system in order to manage building up in the said system of the new total pressure, a partial steam pressure plus support pressure by air, upholding an accurate control about a balance position, from the saturation pressure of the steam, which pressure has controlled the regulation during the heating period. In the described embodiment such a system is provided by supply of air through the bypass conduit 23 with the valve 25 and the pressostat 62, which is dependent upon the pressure in the chamber 10 at the point 64. To obtain stability of the system the regulator 54 is adjusted with a very great constant of proportionality, whereas small constants are set for the regulators 58 and 66.

When the valve 25 is open and supplies the chamber with a suitable support pressure, the pressostat 62 operates intermittently at this pressure. Steam supplied through the valve 18 works against the entire support pressure and thus the medium entering the chamber has a higher temperature than the intended sterilization temperature. However, this affects the regulator 58 so that it starts the supply of air through the valve 22. The magnitude of the support pressure controlled by the pressostat is such that the pressure is exactly sufficient to open the valve 50, which by the regulator 66 is operated by the pressure in the chamber at the sensing body 68. Thereafter, the supply of air will not take part in controlling the process until the objects in the chamber are to be cooled during the after treatment, when the sterilization process is achieved.

As stated hereinabove, the steam supplied works against the entire support pressure. If the steam is permitted to do so without control, this will cause an unstable temperature control in the chamber at low temperatures. To avoid this drawback the system is designed so that the steam supply valve 18 is operated by the regulator 54, which is controlled by the temperature at the sensing body 56 located downstream of the valve 18. This regulator is adjusted to close the valve at a temperature which is 10° to 15° higher than the temperature at the sensing body 60, which controls the air supply regulator 58.

In a practical application of the present invention, it has proved to be possible and without risk, to keep a treatment temperature in the chamber which differs by only one degree centrigrade from the temperature that would be intolerable in the packaging material or the products.

Figure 3:
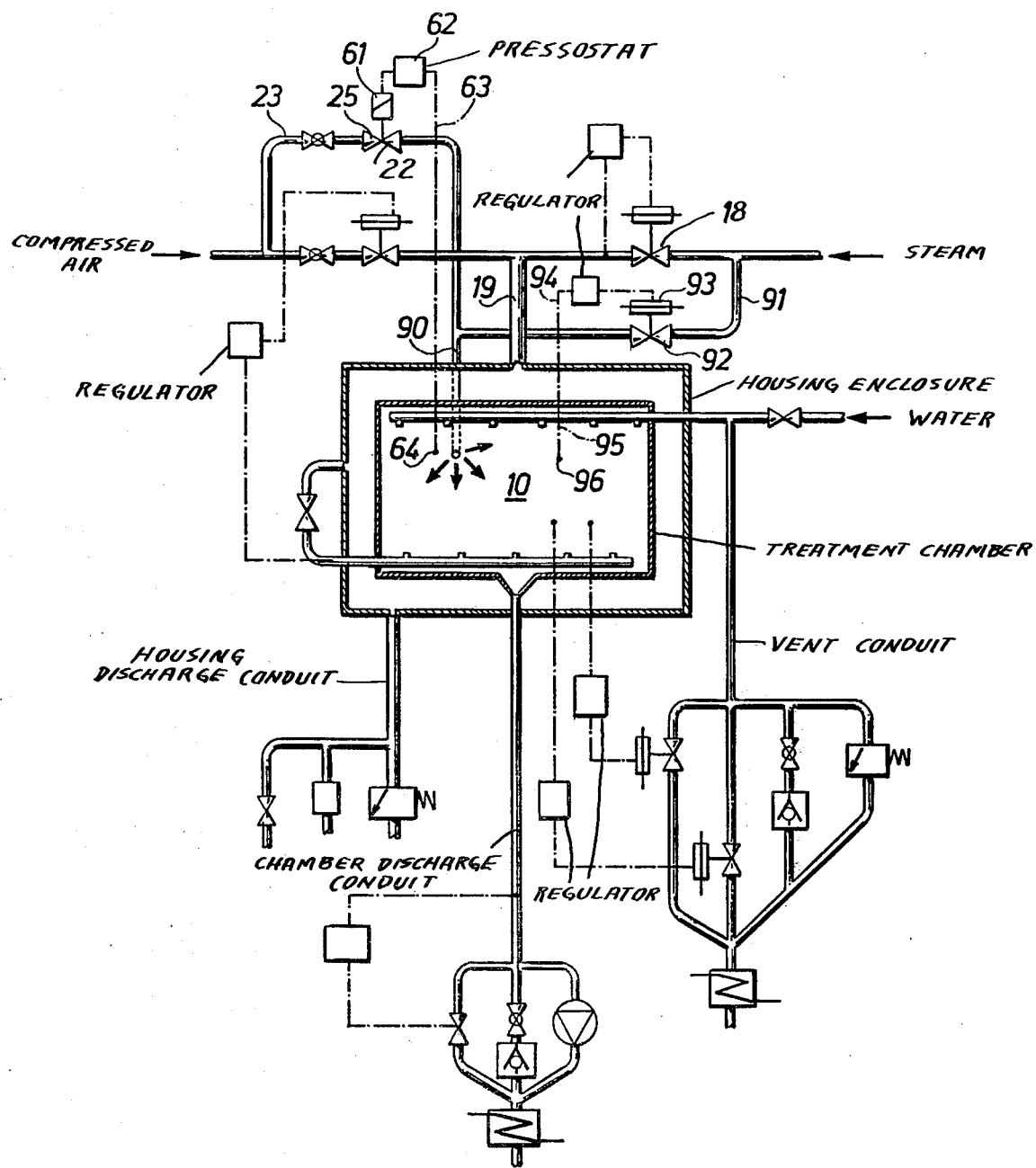
FIG. 3 is the same diagrammatic view as shown in FIG. 1, however with a modification of the supply arrangement to the chamber.

FIG. 3 shows a modified embodiment of the supply of working media to the autoclave of the present invention. It differs from the embodiment of FIG. 1 in that the bypass conduit 23 for compressed air does not enter the mixing chamber 19, as shown in FIG. 1, but passes directly into the autoclave chamber 10 by means of a conduit 90. As stated hereinbefore, compressed air through the conduits 23, 90 is supplied by means of the valve 25, the operating device of which is controlled by the pressostat 62, which by means the conduit 63 is controlled by the temperature at the point 64 in the chamber 10.

In addition to the above modification, there is included a bypass conduit 91 for steam with a valve 92 having operating means controlled by a regulator 94 which by a conduit 95 is controlled by the pressure at a point 96 in the chamber 10. The remainder of the autoclave shown in FIG. 3 corresponds to the autoclave of FIG. 1, except for the fact that in addition to the parts shown in FIG. 2 the system, of course, also has means controlling the regulator 94 in the programmed device 80.

When the sterilization period has been completed, the treatment can be continued in a known manner by pressure reduction, cooling and drying of the items, as well as introduction of sterile air into the chamber. Thereafter, the chamber door can be opened and the objects removed therefrom.

The invention is not limited to the apparatus shown and described and to the method applied in connection therewith but can be modified in many respects within the scope of the following claims. It should be pointed out that the description deals with a particularly favorable embodiment of the autoclave with a chamber for the objects to be treated which is surrounded by a housing. According to the invention, however, in such an autoclave the working media can be conducted past the housing and directly into the chamber. It is also possible to apply the invention to an autoclave without a housing.

What is claimed is:

1. An autoclave for sterilizing objects comprising a chamber, a first supply conduit for steam communicating with said chamber, a second supply conduit for compressed air communicating with said chamber, at least one discharge conduit and at least one vent conduit communicating with said chamber, a first regulating valve in said steam supply conduit, a first regulator controlling said first regulating valve by the temperature in said first conduit downstream of said first regulating valve, a second regulatory valve in said compressed air supply conduit and a second regulator controlling said second regulatory valve by means of the temperature in said chamber, a by-pass conduit for said air supply conduit having a bypass valve, a pressostat operating said bypass valve and being controlled by pressure present in said chamber, said vent conduit and discharge conduit each being provided with a throttle for constant flow therethrough, and a third regulator, said vent conduit further having a valve operated by said third regulator controlled by the pressure in said chamber.

2. An autoclave as claimed in claim 1 further comprising a throttle in said bypass conduit.

3. An autoclave as claimed in claim 1 further comprising an inlet for compressed air and steam located at the bottom of said chamber and an outlet connected to said vent conduit positioned adjacent to the top of said chamber.

4. An autoclave as claimed in claim 1 wherein said first regulator controlling said first regulating valve in the steam conduit is adjustable to a temperature which is 10°–15° higher than the temperature at which said second regulator controlling said second regulatory valve in the compressed air conduit is adjusted to.

5. An autoclave as claimed in claim 1 wherein the first regulating regulator controlling said first regulating valve in the steam conduit is adjustable with respect to the second regulator controlling the second regulatory valve in the compressed air conduit and the third regulator operating said valve in said vent conduit to form a stable dynamic system.

6. An autoclave as claimed in claim 1 further comprising a bypass conduit for steam around said first regulating valve, said bypass conduit having a valve and a regulator, the latter being controlled by the pressure in said chamber and operating said valve in the bypass conduit for steam.

7. An autoclave as claimed in claim 6 wherein said bypass conduit for compressed air communicates with said chamber, and said bypass conduit for steam is connected to said bypass conduit for compressed air.

* * * * *

UNITED STATES PATENT OFFICE
CERTIFICATE OF CORRECTION

PATENT NO. : 4,127,384
DATED : November 28, 1978
INVENTOR(S) : HANS A. FAHLVIK and KURT E. SANDQUIST It is certified that error appears in the above-identified patent and that said Letters Patent are hereby corrected as shown below:

Column 1, line 21, change "ordder" to --order--.

Column 4, line 31, change "conrol" to --control--.

Column 6, line 65, cancel "regulating" first occurrence.

Signed and Sealed this

Tenth Day of April 1979

[SEAL]

Attest:

RUTH C. MASON
Attesting Officer

DONALD W. BANNER
Commissioner of Patents and Trademarks